United States Patent [19]

Fredriksson

[11] 4,034,597

[45] July 12, 1977

[54] METHOD AND APPARATUS FOR MEASURING STEAM QUALITY

[75] Inventor: Oke A. Fredriksson, Fullerton, Calif.

[73] Assignee: Chevron Research Company, San Francisco, Calif.

[21] Appl. No.: 729,245

[22] Filed: Oct. 4, 1976

[51] Int. Cl.² .................. G01K 17/06; G01N 19/10
[52] U.S. Cl. ........................................ 73/29; 73/92
[58] Field of Search .................... 73/29, 192, 193 R

[56] References Cited

U.S. PATENT DOCUMENTS 3,221,541 12/1965 Osborne .......................... 73/29 X
3,430,483 3/1969 Clawson et al. ...................... 73/29

Primary Examiner—James J. Gill
Attorney, Agent, or Firm—R. L. Freeland, Jr.; Edward J. Keeling

[57] ABSTRACT

Method and apparatus for estimating steam quality which involves sampling a steam-water mixture and utilizing volume relationships between the volume of initial sample and volume of the sample when water in sample is converted to steam.

2 Claims, 4 Drawing Figures

METHOD AND APPARATUS FOR MEASURING STEAM QUALITY

FIELD OF THE INVENTION

The present invention relates to determining the approximate quality (i.e., the steam to sample ratio by weight) of steam flowing in a steam line. More particularly, the present invention relates to a method and apparatus for estimating steam quality which involves sampling a steam-water mixture (wet steam) flowing in a steam line and utilizing certain volume relationships between the volume of the sample and the volume of the sample when the water is converted to steam.

BACKGROUND OF THE INVENTION

During generation and use of steam, it is often desirable to know the quality of the steam. Various techniques have evolved for measuring steam quality. The more common of these techniques involve using various colorimeters and orifice meters. Other techniques are available utilizing properties of feed water compared to the properties of the liquid phase of the steam. A discussion of these techniques is given in U.S. Pat. No. 3,596,516, issued Aug. 3, 1971. There is still need, however, for a method and apparatus for readily determining the quality of steam.

BRIEF DESCRIPTION OF THE INVENTION

The present invention relates to estimating the quality of wet steam flowing in a steam line by first establishing a sample chamber within the steam line. The sample chamber is opened to wet steam flowing in the steam line to fill a known first volume of the sample chamber with a representative portion of the wet steam flowing in steam line at the same temperature and pressure as the wet steam flowing in the line. The sample chamber is then closed to capture the representative portion of wet steam containing a liquid portion and a gaseous portion in the sample chamber. The volume of the closed sample chamber is then increased to allow evaporation of the liquid portion of the representative portion of wet steam while continuing to flow wet steam in the steam line past the sample chamber to maintain the temperature in the sample chamber substantially the same as the temperature of the wet steam in the steam line. The pressure in the closed sample chamber is observed while the volume of the closed sample chamber is continuing to increase the volume of the closed sample chamber to allow evaporation of substantially all of the liquid portion of the representative portion while simultaneously observing the volumetric increase in the closed sample chamber. The volumetric increase in the closed sample chamber is recorded at the time the pressure in the sample chamber begins to decrease below its initial value which indicates the evaporation of substantially all of the liquid portion of the representative portion. The approximate quality of the wet steam flowing in the steam line is then determined by the ratio of the volumetric increase in the sample chamber over the first volume of the sample chamber.

The invention provides steam quality measuring apparatus for use in determining steam quality in a line containing wet steam. A sample chamber is positioned in the steam line in position to take a representative sample of wet steam flowing in the line while permitting a substantial portion of the wet steam flowing in the line to bypass the sample chamber. Valve means are provided for opening the sample chamber to capture therein a sample of wet steam containing a liquid portion and a gaseous portion. Means are also provided for closing the sample chamber after a known volume of sample is captured therein. Means are provided for increasing the volume of the sample chamber, and for measuring the volume increase. A pressure indicator is used for monitoring the pressure in the sample chamber.

PRINCIPAL OBJECT OF THE INVENTION

The principal object of the present invention is to provide a method and apparatus for estimating steam quality by utilizing certain volume relationships in a sample of the wet steam between the volume of steam and the volume of the water content of the wet steam when converted to steam. Additional objects and advantages of the present invention will become apparent from a detailed reading of the specification and drawing which are incorporated herein and made a part of this specification.

BRIEF DESCRIPTION OF THE DRAWINGS

FIG. 4 is a sectional view taken at line 4—4 of FIG. 1.

DESCRIPTION OF PREFERRED EMBODIMENT

Figure 1:
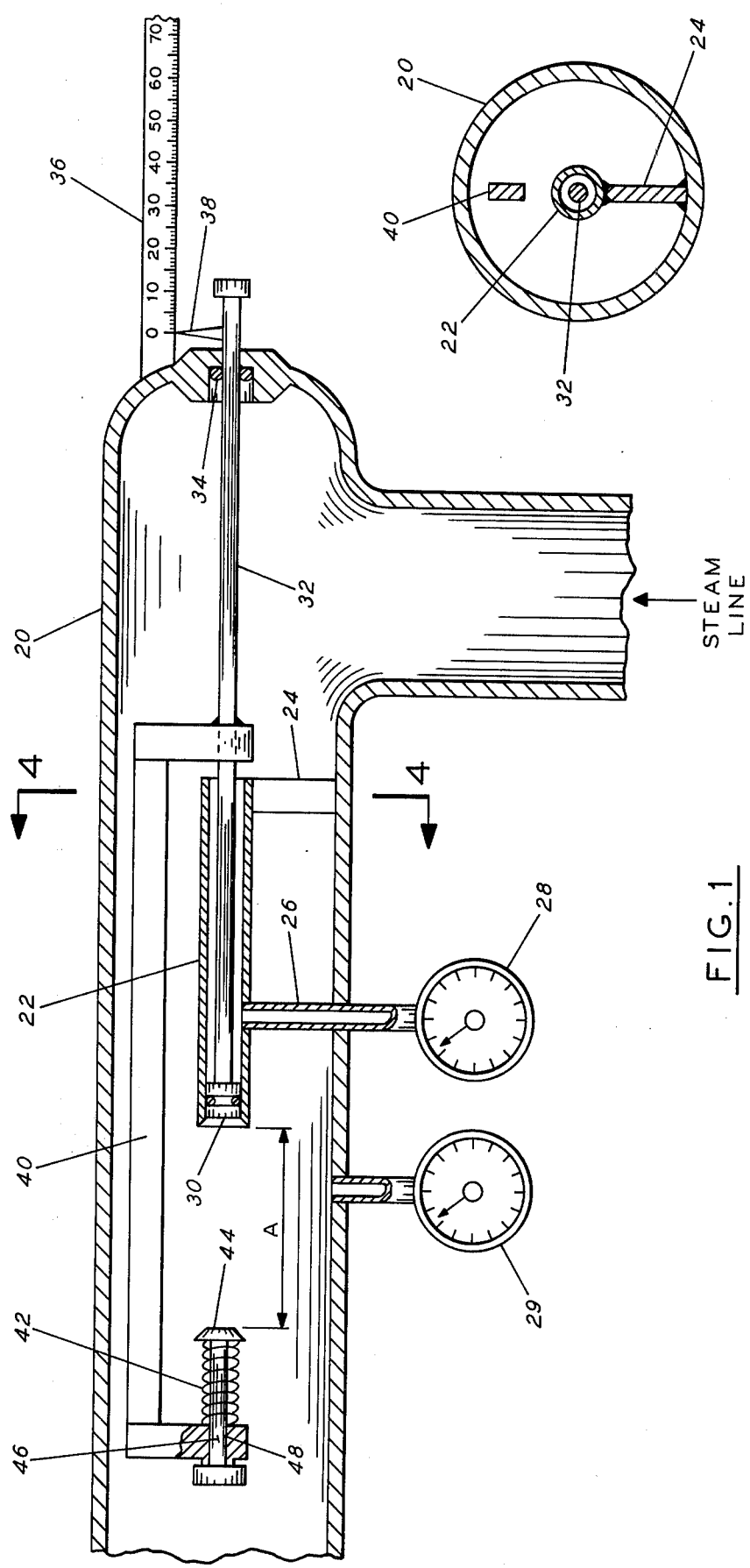
FIG. 1 is an elevation view with portions broken away for clarity of presentation and illustrates the preferred embodiment of apparatus assembled in accordance with the present invention in position to begin taking a sample.

FIGS. 1 and 4 schematically illustrate the preferred embodiment of apparatus in position to begin taking a sample of wet steam flowing in steam line 20. A sample chamber 22 is connected interiorly of steam line 20. Thus stabilizing fin 24 and the conduit 26 to pressure gauge 28 are utilized to fixedly connect sample chamber inside of steam line 20 in a manner so that steam may flow along the longitudinal axis of the sample chamber. A piston 30 having a suitable O-ring initially prevents wet steam from entering into sample chamber 22. The piston 30 is fastened to a shaft 32 which extends through packing gland 34 to the outside of the steam line 20. An indicator 36 is fastened external to the steam line and pointer 38 on shaft 32 permits measurement of the position of the piston 30 in the sample chamber. A bracket 40 is rigidly connected to the shaft 32 for travel therewith and is equipped with a spring 42 loaded valve 44 whose stem 46 is free to move in a sleeve 48 of the bracket. A second pressure gauge 29 may be utilized to obtain a pressure reading in the steam line. The valve 44 of course travels with the bracket 40 and the shaft 32. It will travel through the distance A when the shaft is withdrawn to open the sample chamber 22 to wet steam as the piston 30 is moved up into the chamber.

Figure 2:
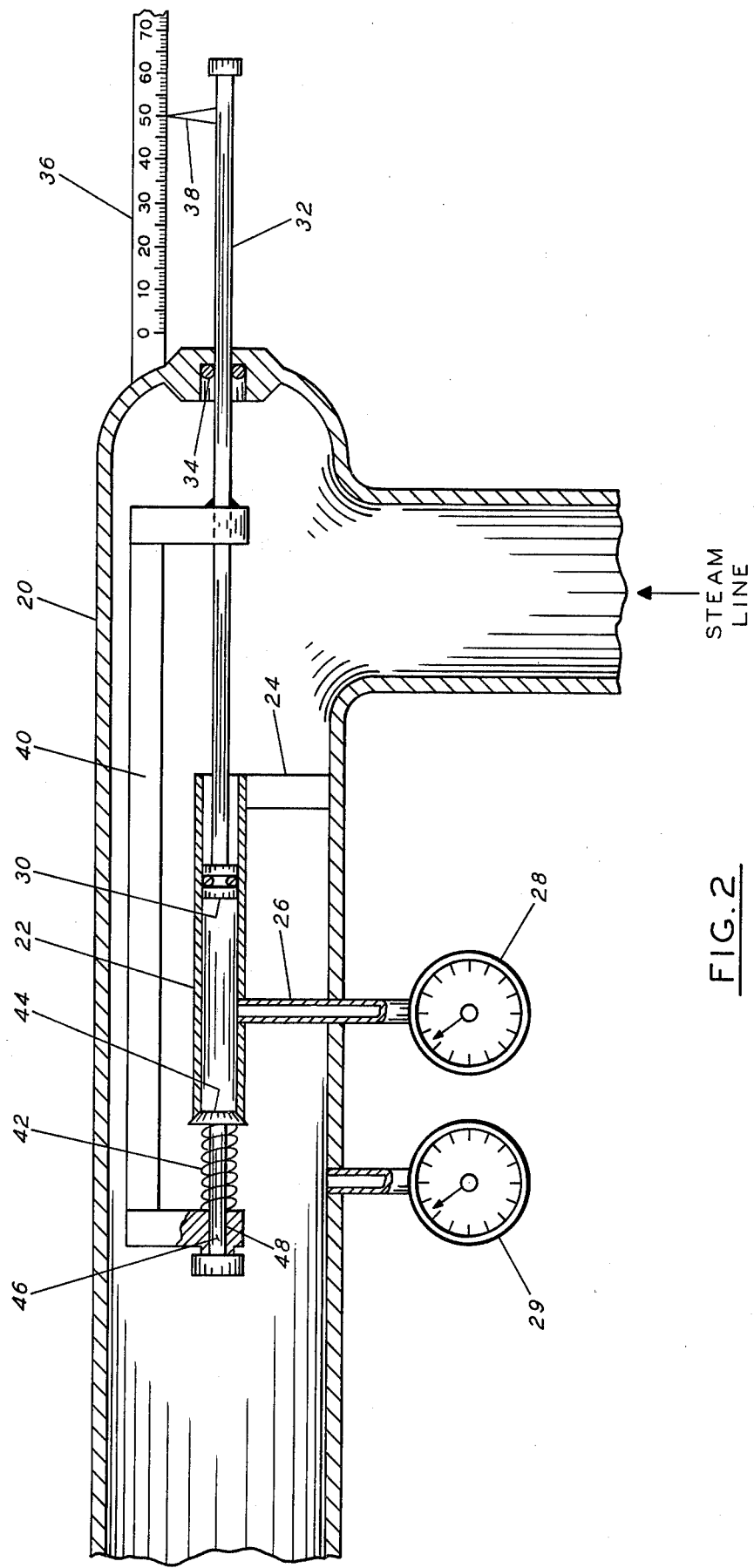
FIG. 2 is an elevation view with portions broken away for clarity of presentation and illustrates the preferred embodiment of apparatus assembled in accordance with the present invention just after capturing a sample.

FIG. 2 illustrates the apparatus of the present invention after the shaft 32 has been withdrawn the A distance. The valve 44 has just seated in the valve seat of sample chamber 22 to close the sample chamber. If the A distance for example was 50 cm and the piston head and the inside of the sample chamber 1 cm² then a sample of 50 cm³ volume of wet steam would be taken when the apparatus is in the position of FIG. 2. At this position the pressure on gauges 28 and 29 indicating the pressure in the sample chamber and the steam line will be equal.

Figure 3:
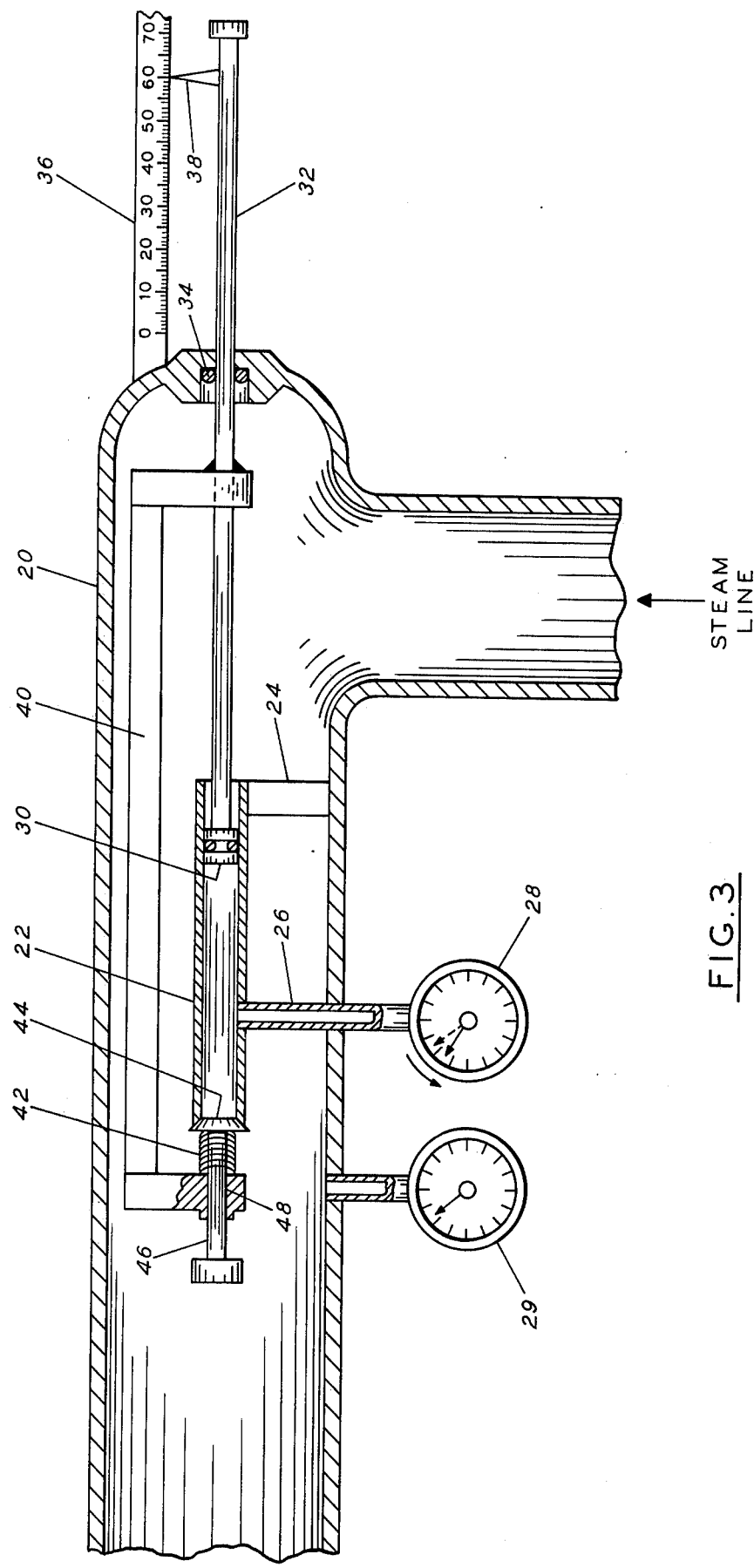
FIG. 3 is an elevation view with portions broken away for clarity of presentation and illustrates the preferred embodiment of apparatus assembled in accordance with the present invention in a position where evaporation of the water content of the sample has just occured.

As the piston 30 is moved to increase the volume of the now closed sample chamber beyond 50 cm³ the pressures inside the sample chamber 22 and inside the steam line 20 will remain very nearly the same until the liquid portion of the wet steam sample has been converted into steam. The heat required to produce this conversion is supplied by the steam flowing past the sample chamber and in contact with the piston and the valve. As noted in FIG. 3 and withdrawal of the piston 30 beyond the point where the liquid portion of the sample has evaporated will produce a significant pressure drop in the sample chamber which is observed on pressure gauge 28. Thus, the volumetric increase required to evaporate the liquid can be noted by reading the distance the pointer has moved after the sample chamber was just closed (FIG. 2) until a pressure drop was noted in gauge 28 (FIG. 3). If, for example, with a 50 cm³ sample and the 1 cm² piston a reading of 60 cm on the indicator would indicate a liquid quantity by weight of approximately 20% the steam quantity by weight or a steam weight to total sample weight of approximately 83%.

The theoretical basis for the present invention is given below.
Let
V = a volume occupied by the water steam mixture
$V_s$ = the volume occupied by the steam
$V_w$ = the volume occupied by the water
$\rho_s$ = the steam density at some constant pressure and temperature (P and T)
$\rho_w$ = the water density at some constant pressure and temperature (P and T)
$R_x$ = steam-to-sample ratio by weight
$V_f$ = final volume after the water has been converted to steam
Now $$R_x = \frac{\rho_s V_s}{\rho_s V_s + \rho_w V_w}$$

The water expanded into steam, at P and T, will occupy a volume $\Delta X$, $$\Delta X \rho_s = \rho_w V_w$$

Therefore $$R_x = \frac{\rho_s V_s}{\rho_s V_s + \rho_s \Delta X} = \frac{V_s}{V_s + \Delta X}$$

Since $$V_f = V_s + \Delta X,$$

$$R_x = V_s/V_f.$$

(Under the conditions when $$V_s \cong V$$

$$R_x \cong V/V_f,$$

the percent steam quality is approximately equal to $V/V_f \times 100\%$.)

Now $$\Delta X - V_w = V_f - V \text{ or}$$

$$\frac{\rho_w}{\rho_s} V_w - V_w = V_f - V = V_w \left( \frac{\rho_w - \rho_s}{\rho_s} \right)$$

$$V_w = \frac{\rho_s(V_f - V)}{\rho_w - \rho_s}.$$

$$V_f = V_s + \Delta X = V_s + \frac{\rho_w}{\rho_s} V_w$$

$$V_s = V_f - \frac{\rho_w}{\rho_s} \times \frac{\rho_s(V_f - V)}{\rho_w - \rho_s}$$

$$R_x = \frac{V_f - \frac{\rho_w(V_f - V)}{\rho_w - \rho_s}}{V_f}$$

$$R_x = 1 - \frac{\rho_w(V_f - V)}{V_f(\rho_w - \rho_s)}$$

and the percent steam quality is equal to $$100 \left[ 1 - \frac{\rho_w(V_f - V)}{V_f(\rho_w - \rho_s)} \right]\%$$

The values of $\rho_w$ and $\rho_s$ at a particular P and T is obtained from handbook tables such as contained in the Crane Co. Technical Paper No. 409, dated 1942, titled "Flow of Fluids Through Valves, Fittings, and Pipe".

A differential pressure, $\Delta P$, between gauges (28 and 29) will be noted if the piston (30) has been moved too far. Assume the captured dry steam at constant temperature now behaves as an ideal gas. The volume of captured steam is directly proportional to the total travel, D, of the piston noted on the indicator (36). Let P equal the pressured noted on gauge (29). Then $$D(P-\Delta P) = P(D-\Delta D)$$

wherein $\Delta D$ is the distance of overtravel of the piston (30) and $$\Delta D = D(\Delta P/P)$$

$\Delta D$ permits calculating the distance the piston should have been moved to just allow all water to be coverted to steam and therefore permit determination of the steam quality.

In summary, a method and apparatus has been described for measuring steam quality utilizing volume relationships between an initial sample and the sample when the liquid phase has been converted to vapor. Other modifications and variations of the present invention as set out herein may be made without departing from the spirit thereof and such modifications are meant to be included in the appended claims.

What is claimed is:
1. A method of estimating the quality of wet steam in a steam line comprising flowing wet steam in a steam line, establishing a sample chamber within said steam line, opening said sample chamber to wet steam flowing in said steam line to fill a known first volume of said sample chamber with a representative portion of the wet steam flowing in said steam line at the same temperature and pressure as the steam flowing in said line, closing said sample chamber to capture said representative portion of wet steam containing a liquid portion and a gaseous portion in said sample chamber, increasing the volume of said closed sample chamber to allow evaporation of the liquid portion of said representative portion while continuing to flow wet steam in said steam line past said closed sample chamber to maintain the temperature in said closed sample chamber substantially the same as the temperature of the wet steam in said steam line, observing the pressure in said closed sample chamber while continuing to increase the volume of said closed sample chamber to allow evaporation of substantially all of the liquid portion of said representative portion while simultaneously observing the volumetric increase in said closed sample chamber, noting the volumetric increase in said closed sample chamber at the time the pressure in said closed sample chamber begins to decrease its initial value indicating evaporation of substantially all of the liquid portion of said representative portion and determining the approximate quality of wet steam flowing in said steam line by establishing the ratio of said volumetric increase in said closed sample chamber to said first volume of said sample chamber.

2. Steam quality measuring apparatus for use in determining steam quality in a steam line containing wet steam comprising a steam line, a sample chamber positioned in said steam line to permit taking a representative sample of steam flowing in said line while permitting a substantial portion of the steam flowing in said steam line to bypass said sample chamber, means for opening said sample chamber to capture therein a sample of steam containing a liquid portion and a gaseous portion, means for closing said sample chamber after a known volume of sample is captured therein, means for increasing the volume of said closed sample chamber above said known volume, measuring means for measuring said volume increase, and means for measuring the pressure in said closed sample chamber as the volume of said sample chamber is increased.

* * * * *